United States Patent
Ihme et al.

(10) Patent No.: US 7,062,319 B1
(45) Date of Patent: Jun. 13, 2006

(54) METHOD AND ARRANGEMENT FOR DETERMINING SUITABLE TREATMENT FREQUENCY AND/OR INTENSITY

(75) Inventors: Jouni Ihme, Jääli (FI); Riitta Vesikukka, Oulu (FI)

(73) Assignee: Innokas Medical Oy, Kempele (FI)

( * ) Notice: Subject to any disclaimer, the term of this patent is extended or adjusted under 35 U.S.C. 154(b) by 499 days.

(21) Appl. No.: 10/130,359

(22) PCT Filed: Nov. 17, 2000

(86) PCT No.: PCT/FI00/01011

§ 371 (c)(1),
(2), (4) Date: Oct. 4, 2002

(87) PCT Pub. No.: WO01/36038

PCT Pub. Date: May 25, 2001

(30) Foreign Application Priority Data

Nov. 17, 1999 (FI) .................................. 19992469

(51) Int. Cl.
*A61N 1/32* (2006.01)
(52) U.S. Cl. ............................................ 607/2; 607/66
(58) Field of Classification Search ................ 600/554; 607/39–58, 66
See application file for complete search history.

(56) References Cited

U.S. PATENT DOCUMENTS 5,806,522 A * 9/1998 Katims ........................ 600/554
6,161,044 A * 12/2000 Silverstone .................. 607/45

FOREIGN PATENT DOCUMENTS

JP         404132565 A   *  5/1992
WO     WO 94/25103 A1   *  4/1993

* cited by examiner

*Primary Examiner*—Carl Layno
(74) *Attorney, Agent, or Firm*—Young & Thompson

(57) ABSTRACT

A method and arrangement for determining a suitable treatment frequency and/or intensity of a treatment signal used in electrical treatment. In the method, a stimulating electrical signal is directed to an object to produce different reaction types in the object at different intensities of the stimulating electrical signal. For at least three different reaction types, the intensity of the stimulating electrical signal at which a reaction type occurred is stored. The electrical signal intensities stored for the different reaction types at least at three different frequencies are compared with reference values and the frequency and/or signal intensity at which the signal intensity deviates sufficiently from one or more reference values is determined. The method utilizes the frequency and/or signal intensity found in the process in determining the suitable treatment frequency and/or signal intensity.

4 Claims, 5 Drawing Sheets

METHOD AND ARRANGEMENT FOR DETERMINING SUITABLE TREATMENT FREQUENCY AND/OR INTENSITY

BACKGROUND OF THE INVENTION

The invention relates to a method for determining a suitable treatment frequency and/or intensity of a treatment signal used in electrical treatment.

The invention also relates to an arrangement for determining a suitable treatment frequency and/or intensity of a treatment signal used in electrical treatment.

The invention is applied in determining a best possible treatment frequency and/or intensity before the actual treatment administered by an electrical treatment device. The method may also be repeated after the treatment in order to determine whether or not the treatment has been effective; previously, it has been impossible to analyze treatment parameters.

The known solutions in the field utilize values that through research or experience are believed to be suitable for adjusting the intensity and frequency of the treatment current. The known solutions are also unable to state the effect of the treatment afterwards in any other way than by interviewing the patient. The researched and empirical information and employing this information have resulted in the fact that the decision made by an administrator of the treatment is not based on the patient's acute state or thorough examination of the patient's problem but the treatment parameters are determined more or less approximately. The efficiency and quality of treatment are at least questionable. The information on the effects of the treatment based on the patient's feelings is relative and thus incomplete, so whether or not the treatment has been useful cannot be ascertained. The above-mentioned facts are thus serious drawbacks in the known solutions.

BRIEF DESCRIPTION OF THE INVENTION

An object of the invention is thus to provide an improved method and measurement arrangement to avoid problems and drawbacks associated with the known solutions.

To achieve the object disclosed above, the method of the invention is characterized by directing a stimulating electrical signal to an object to produce different reaction types in the object at different intensities of the stimulating electrical signal, storing for at least three different reaction types the intensity of the stimulating electrical signal at which a reaction type occurred, comparing with reference values the electrical signal intensities stored for the different reaction types at least at three different frequencies, determining the frequency and/or intensity of the signal at which the intensity of the signal deviates sufficiently from one or more reference values, and utilizing the frequency and/or signal intensity found in the process in determining the suitable treatment frequency and/or intensity of the signal.

The arrangement of the invention, in turn, is characterized in that the arrangement comprises a generator to generate treatment current, an intensity adjuster coupled to the treatment current generator for changing the treatment current intensity, a frequency adjuster for the treatment current of the treatment current generator coupled to the treatment current generator and for using at least three different frequencies, a reaction registering device for indicating occurrence of reactions caused by the treatment current, a storing device operatively connected to the reaction registering device wherein the treatment current intensity value that prevailed at the moment of occurrence of a reaction can be stored, a comparing element operatively connected to the storing device for comparing with reference values the electrical signal intensities stored for the different reaction types at least at three different frequencies, and an information display device operatively connected to the comparing element for indicating the frequency and/or signal intensity that has been found suitable to provide an adequately large deviation from one or more reference values. The structural parts mentioned above may be located in the same casing as the treatment current generator, i.e. in the treatment device itself, but in a preferred embodiment, one or more aforementioned structural parts are located in a part called a controller or such a separate part communicating through a cable, wirelessly or otherwise with the treatment device or other such device comprising the treatment current generator.

The background of the invention lies in the physiological structure of a patient and in different frequency responses in tissues in regard to motoric, neurological and tactile sensations. As a final result, the algorithm of the method yields e.g. a matrix wherefrom the treatment current intensity and the treatment frequency can be inferred easily. In an embodiment, the invention can be implemented by utilizing a treatment current intensity adjuster, each step being acknowledged from the same adjuster as well as the treatment current adjustment also being carried out from the same adjuster. Using the algorithm, the matrix and the intensity of the final treatment frequency as well as the treatment current may be calculated unambiguously by a program located in the controller, treatment current generator or a computer.

An advantage of the method and arrangement of the invention is particularly that the invention enables to determine values of the intensity and frequency of the treatment current necessary for the treatment, so the invention thus promotes the treatment event and makes it an efficient and high-quality procedure. It is easy and quick to determine the treatment parameters, i.e. to carry out the method. Since the method is based on the physiological facts, it is easy for the medical staff to understand what the method deals with.

A second target of the invention is a method and arrangement for monitoring the effect of electrical treatment delivered to a trigger point or another point in an object. The known solutions in the field are based on empirical information about a suitable termination point of the treatment and, on the other hand, on monitoring the receiver of treatment using the senses.

The method according to the second target of the invention is characterized by monitoring the increase in a treatment current, and when an adequately rapid change in the increase of the treatment current is detected, an indication is given that a sufficient treatment effect has been achieved.

The arrangement according to the second target of the invention is characterized in that the arrangement comprises means for monitoring the rate of change in a treatment current, and means connected thereto for indicating that an adequately rapid change has occurred, designating a sufficient effect of the treatment.

BRIEF DESCRIPTION OF THE DRAWINGS

The invention is now described in closer detail in connection with the preferred embodiments and with reference to the accompanying drawings, in which.

DETAILED DESCRIPTION OF THE INVENTION

Figure 1:
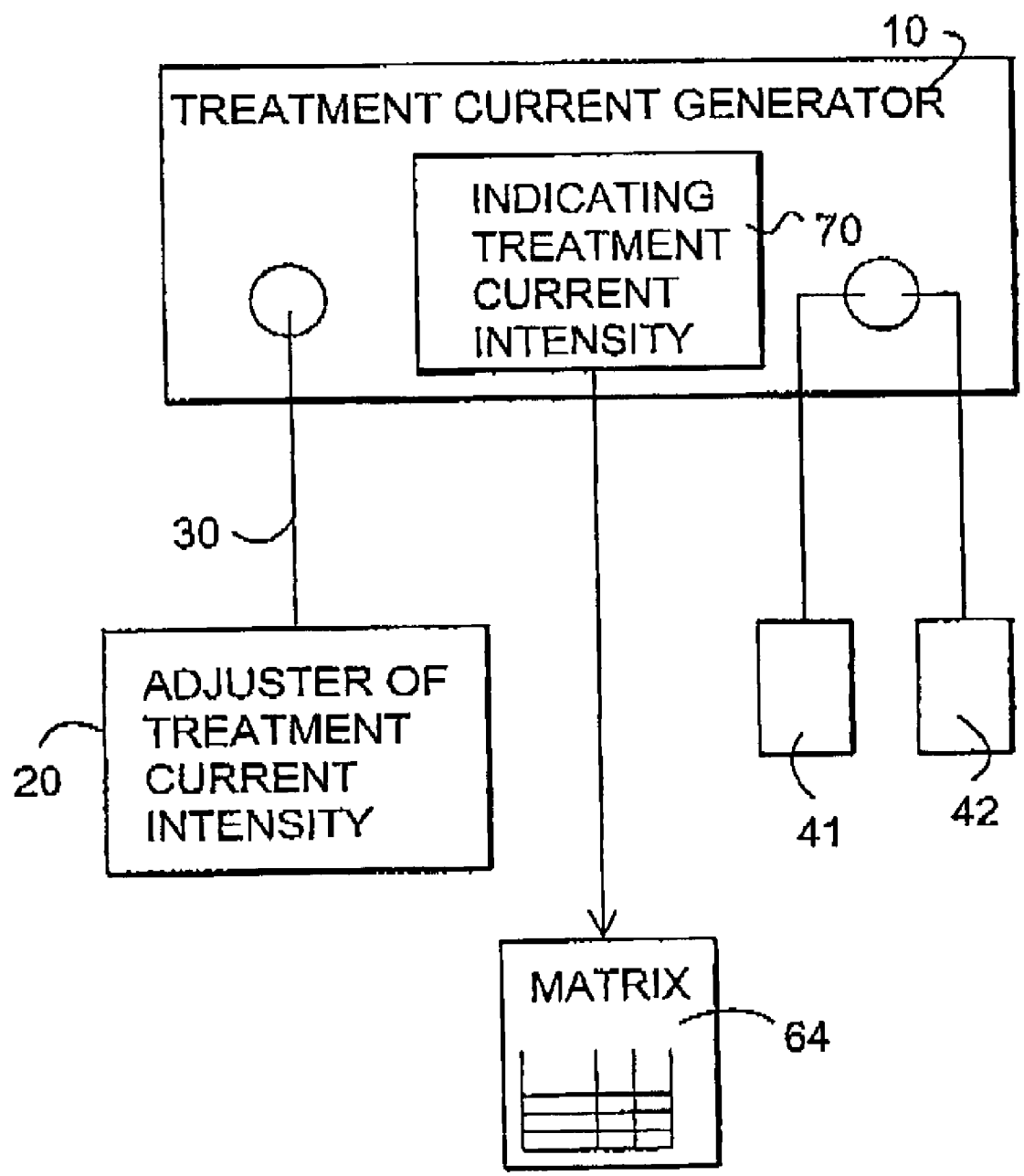
FIG. 1 is a block diagram showing an arrangement according to a first target of the invention.
Figure 2:
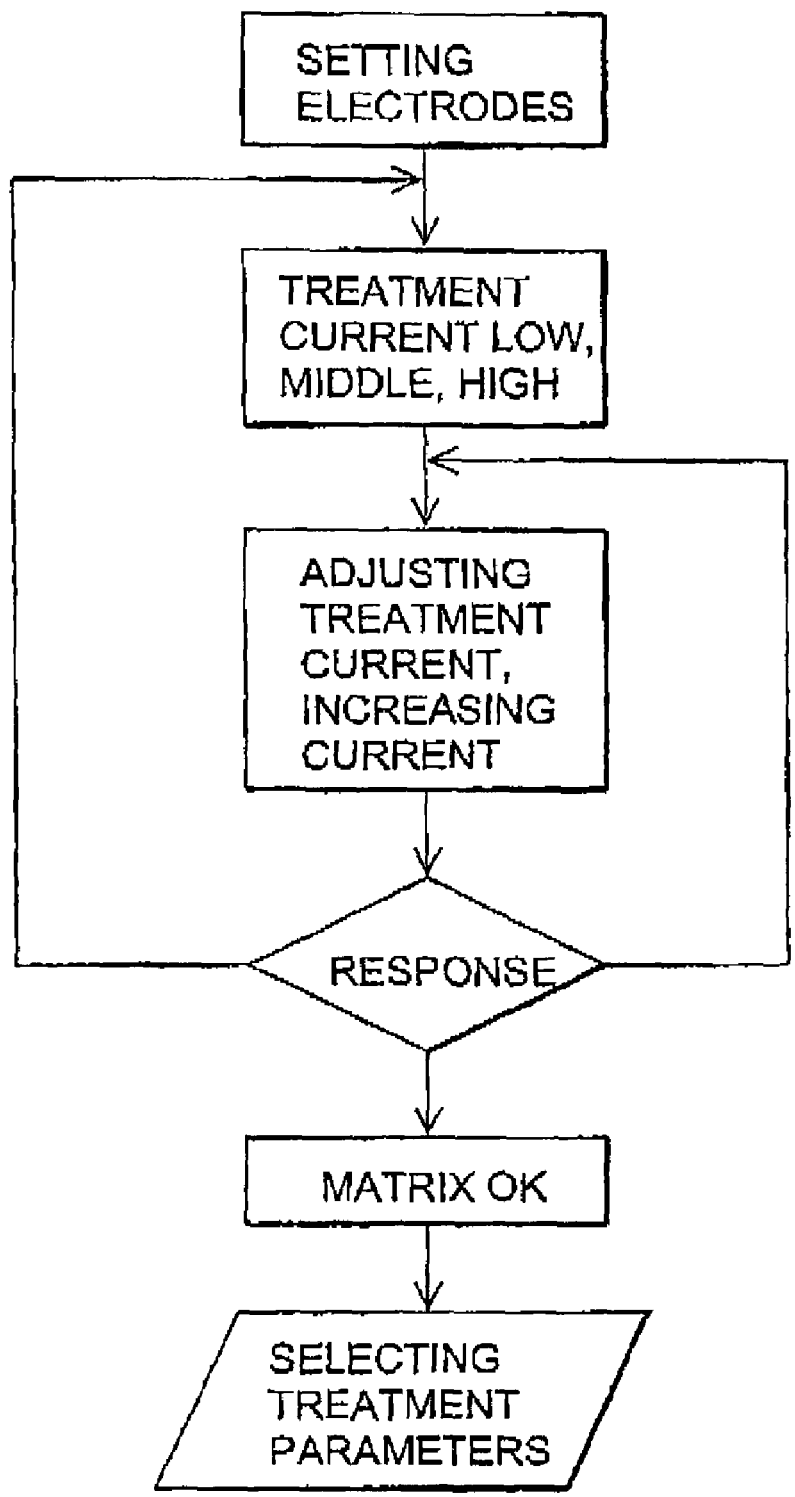
FIG. 2 is a flow diagram showing a method according to the first target of the invention.

FIG. 1 is a block diagram showing an arrangement according to a first target of the invention. The arrangement of FIG. 1 is used for determining a suitable treatment frequency and/or intensity of a treatment signal used in electrical treatment.

FIG. 1 shows a treatment current generator 10, which is part of the arrangement or a part that can be connected to the arrangement. The arrangement comprises a controller 20 connected to the treatment current generator by a cable 30.

The arrangement further comprises an electrode structure 41–42, which comes into contact with an object 45, preferably against a human body or a part thereof. The electrodes are placed either on the ankles or the wrists, according to the symptom.

The treatment current generator 10 may be either an alternating current generator or a direct current generator. In the case of alternating current, the electrode 41 is a "neutral" electrode and the electrode 42 is a "phase" electrode. In the case of direct current, the electrode 41 is a minus (−) electrode and the electrode 42 is a plus (+) electrode. The treatment current generated by the treatment current generator 10 is delivered to the object, such as a person, by the electrode structure 41–42.

The arrangement further comprises an intensity adjuster 61 in connection with the treatment current generator 10 for changing the intensity of the treatment current, and a frequency adjuster for the treatment current of the treatment current generator in connection with the treatment current generator 10 for using at least three different frequencies. The increase and/or decrease in the frequency caused by the adjusters 61, 62 may be carried out stepwise or continuously, i.e. the change may take place steplessly.

The adjusters 61 and 62 thus change the intensity and frequency of the treatment current irrespective of the location of the adjusters. The arrangement further comprises a reaction registering device 63 for indicating occurrence of reactions caused by the treatment current, and a storing device 64 operatively connected to the device 63 for registering the reactions wherein the value of the treatment current intensity prevalent at the moment of occurrence of a reaction can be stored. The arrangement further comprises a comparing element 65 operatively connected to the storing device 64 for comparing with reference values the electrical signal intensities stored for the different reaction types in order to detect at which frequency a difference occurs and in which treatment current intensity area the difference occurs, or at least where it starts and/or ends. The adjusters 61, 62 may be e.g. potentiometers, slide controls, push buttons or other such adjusters. Other alternatives are also feasible. The reaction registering device may be e.g. a switch, press key or other such indicating member. Other alternatives are also feasible. The storing device may be e.g. a memory circuit, register or other such storing device. Other alternatives are also feasible.

The arrangement further comprises an information display device 66 operatively connected to the comparing element 65 for indicating the frequency and/or signal intensity at which an adequately large deviation from one or more reference values occurred. The value/values concerned are thus the suitable values that the method/arrangement indicates to the user. Preferably, the method/arrangement presets the frequency and/or current intensity and the user. The information display element 66 may be a liquid crystal display, led display or the like. The comparing element 65 may be e.g. an element implemented by separate components, microcircuit technology or software.

In a preferred embodiment, at least the treatment current intensity adjuster 61 and/or preferably the treatment current frequency adjuster 62 are located in the controller 20 which comprises the treatment generator and which is separate from the treatment device. Preferably, also one or more of the structural parts including the reaction registering device 63, storing device 64, comparing device 65 and information display element are located in the controller 20 which comprises the treatment generator and which is separate from the treatment device. Separately and together, the preferred embodiments make the controller more integrated and versatile, enabling the invention to be applied without radical changes in the treatment device. A method according to another extreme would be to locate the aforementioned structural parts in the same unit as the treatment generator, i.e. in the treatment device. The invention covers all aforementioned versions with their both extremes as well as the versions therebetween. However, the most preferred embodiment is a controller which is equipped with at least some functions and which is separate from the treatment device and which has a cable or wireless connection. The most preferable version comprises all elements 61 to 66.

Referring to block diagram 1 of the arrangement and to flow diagram 2 of the method, it is stated that in an embodiment, the method operates such that a bipolar mode is arranged from the treatment device and the treatment frequency is set low, e.g. about 10 Hz. The starting level for the signal intensity is e.g. 1 mA but it can be selected as desired preferably, however, such that the starting level does not yet cause a reaction in the object 45. The treatment current intensity is increased by means of the treatment current intensity adjuster, and after the occurrence of the first feeling, i.e. reaction, the treatment current intensity is registered and stored by the reaction registering device 63 and the storing device 64. This is continued until all reactions, i.e. feelings and sensations, in Table 1 below have been observed and registered. The procedure is carried out at least at three frequencies, e.g. at frequencies of 10 Hz, 30 Hz and 100 Hz, but they may also be selected otherwise.

Figure 3:
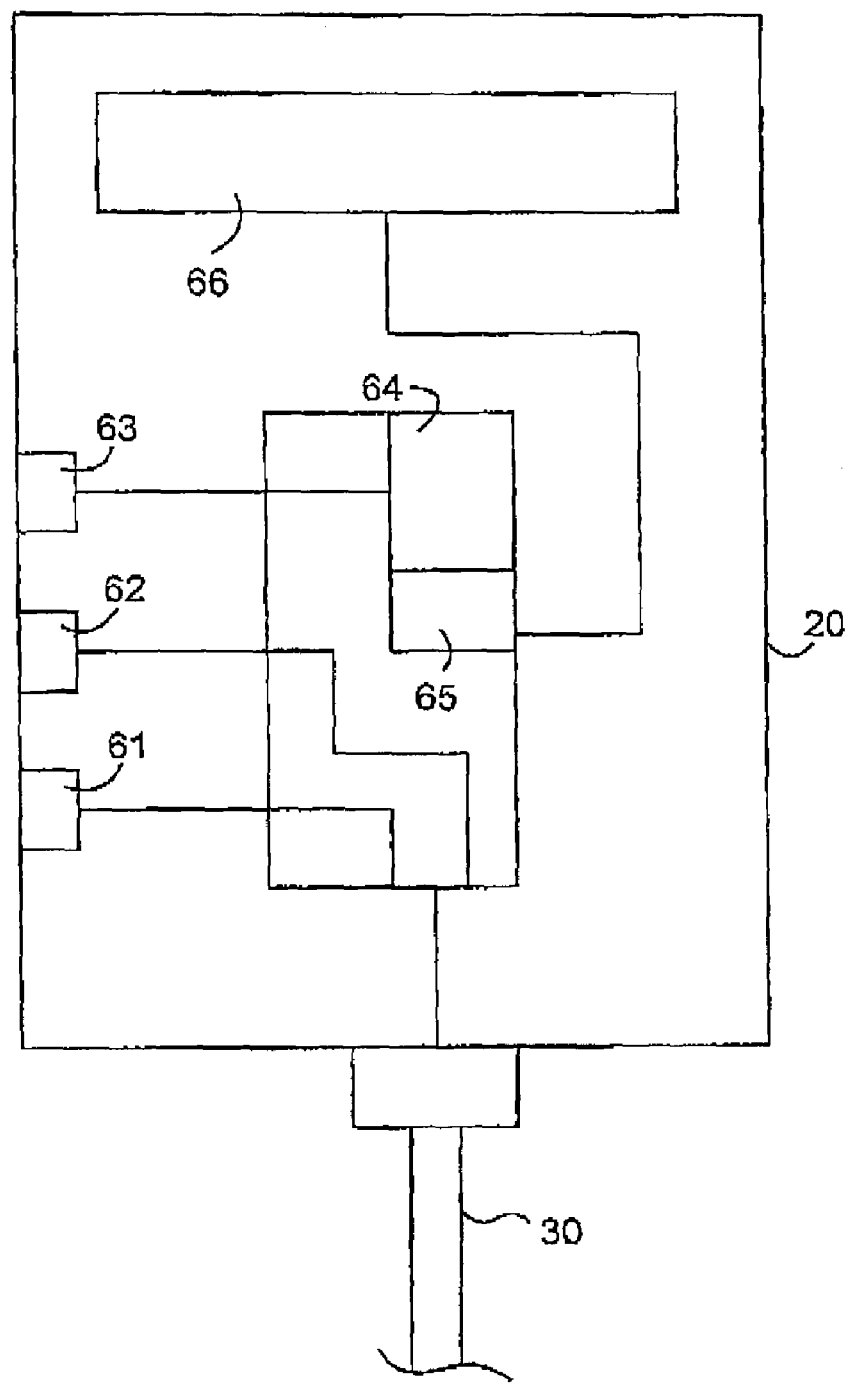
FIG. 3 shows an embodiment of a controller used in the first target of the invention.

In FIG. 1 the designation "matrix" refers to the contents of Table 1, which can thus be considered to be the contents of the storing device 64 of FIG. 3. In FIG. 1, the arrangement comprises a treatment current intensity indicator 70, which thus provides the value of the treatment current prevalent at the registration moment of the reaction, the value being thus stored in the storing device 64 in FIG. 3.

Table 1 shows some measurement results.

TABLE 1

| | Signal intensity (mA) to obtain reaction: | | |
|---|---|---|---|
| Reaction | 10 Hz | 30 Hz | 100 Hz |
| 1 | 9 | 10 | 9 |
| 2 | 11 | 12 | 12 |
| 3A | 14 | 16 | 17 |
| 3B | 16 | 17 | 18 |
| 3C | 18 | 18 | 20 |
| 3D | 21 | 30* | 22 |
| 4 | 26 | 40* | 28 |
| 5 | 30 | 50* | 32 |

Reaction 1: tingle only just perceptible (sensory)
Reaction 2: tingle clearly perceptible (sensory)
Reaction 3A: relatively strong tingle (sensory)
Reaction 3B: strong tingle and weak muscle contraction (motoric)
Reaction 3C: clearly perceptible muscle contraction (motoric)
Reaction 3D: strong muscle contraction (motoric)
Reaction 4: painfully strong muscle contraction
Reaction 5: extreme pain, extremely strong muscle contraction.

When preferably the whole procedure has been carried out, i.e. at all, e.g. three, frequencies used, the algorithm in the comparing device 65 infers the most suitable treatment frequency and treatment current intensity for the treatment from the information stored in the storing device 64, i.e. the information according to Table 1, by comparing the registered results with "standard" values or other such reference values. Alternatively, in another preferred embodiment, the comparing procedure may be carried out already when measurements to be carried out at a particular frequency have been completed. As to the comparing procedure, it is thus stated that it can take place either after the measurements at all, e.g. three, frequencies have been completed, or already after the measurements carried out at each frequency have been completed.

The comparing procedure preferably determines the greatest deviation between the measured value and reference value.

A reference value is e.g. a signal intensity value indicated by experience or practical measurements that should apply in the case of a healthy object. The actual treatment is carried out after the method. The treatment could use a frequency of 30 Hz, the treatment intensity at first being 30 mA, i.e. the starting treatment intensity would at least roughly be the same as the first signal intensity to sufficiently deviate from the reference value in the above-described method for determining the frequency and/or signal intensity. In the example of the table, the reference values in the three lowest classes would be about 20, 27 and 30, from which measured values 30, 40 and 50 considerably differ since the defect in the object prevents the object from giving a response until at "too high" treatment current intensities.

A reference value may also be a value measured from the object itself, i.e. a value measured from a paravertebrally healthy side, i.e. from the other side of the body than the side receiving treatment and thus, in accordance with the invention, the place needing the treatment frequency and/or treatment current intensity to be determined. This means that if the defect in a patient is on the right side, e.g. in the right hand, the reference values for the paravertebral side are obtained from measurements carried out from the left hand.

The method thus determines the frequency and/or signal intensity at which the signal intensity sufficiently deviates from one or two reference values. The method employs the frequency and/or signal intensity found in the procedure in determining a suitable treatment frequency and/or signal intensity. This means that the value searched for may as such already be the value that will be used in the treatment, or the value searched for serves as a suggestive value. As to the frequency the situation is simple, i.e. in a preferred embodiment, a suitable treatment frequency will be exactly the frequency at which the deviation occurred. In a preferred embodiment, the suitable treatment current intensity is the intensity at which the deviation first occurred. In the exemplary case, the frequency value obtained on the basis of Table 1 would be 30 Hz, and the suitable current intensity value would be 30 mA, wherefrom the intensity can be increased. After the treatment, the method can be repeated to state whether or not the treatment has been useful.

Figure 4:
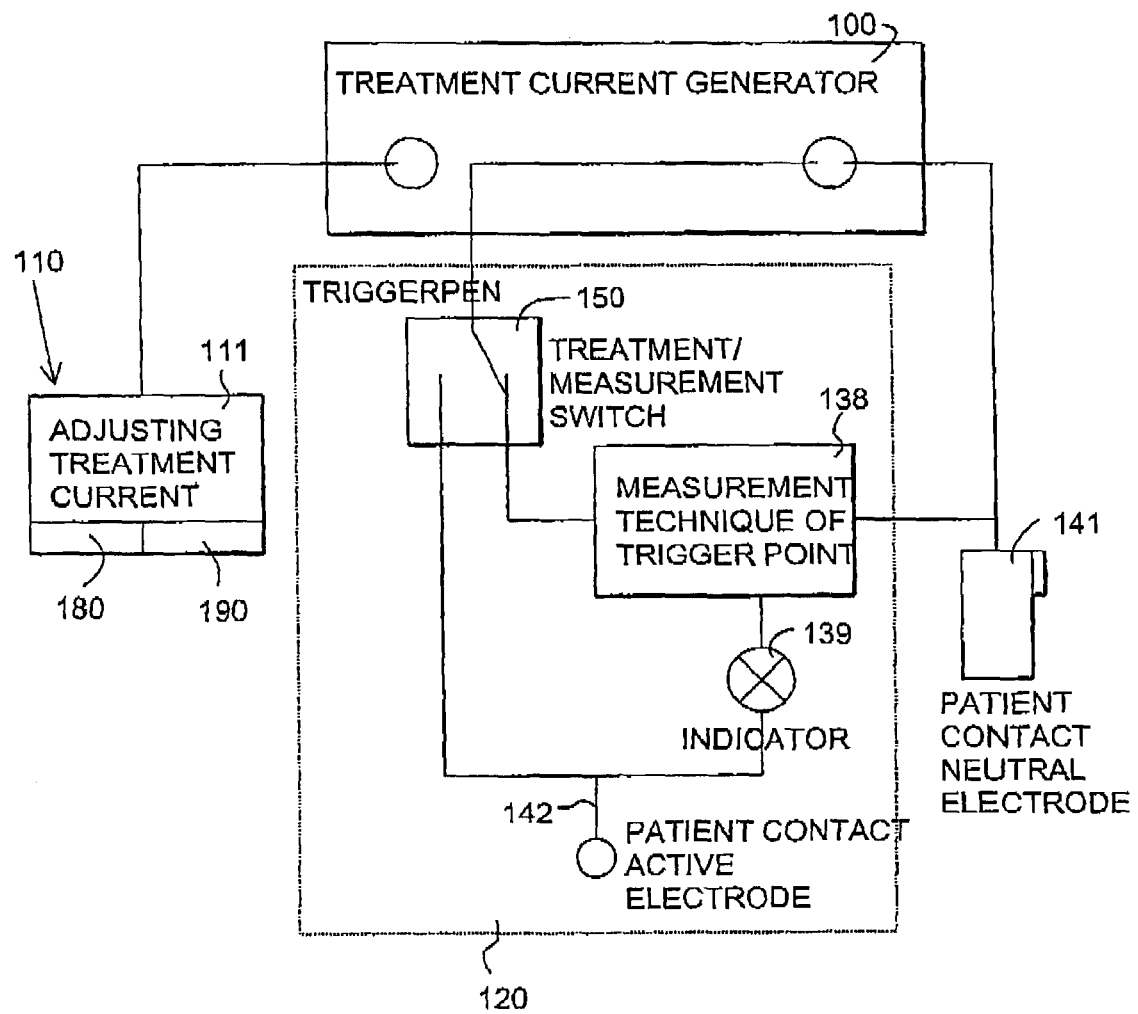
FIG. 4 is a block diagram showing an arrangement of a second target of the invention.

FIG. 4 is a block diagram showing an arrangement according to a second target of the invention. In the second target of the invention, the method comprises monitoring indirectly the effect of manipulating the trigger point of the object. First, by using a pen-like or other such auxiliary means 120, the point whereto it would be advantageous to deliver electric treatment current is accurately located. When the electric treatment current is delivered exactly to the point determined by the method, the treatment effect of the electric treatment current can be optimized and the treatment takes place as "precision treatment" deep inside the object to be treated and within the problematic area, thus eliminating the problem and making the symptoms disappear in the best possible manner. In other words, a neutral contact is attached to the object, such as a human patient, typically by means of a neutral electrode. Treatment current is generated between the neutral contact 141 and an electrode 142 of the pen-like or other such auxiliary means 120 by a generator 100 comprising a current output. The pen-like or other such auxiliary means 120 is switched by a switch 150 to a measuring position (the switch is turned to the right) and the auxiliary means 120 is then moved on the patient's skin until the auxiliary means 120 indicates by means of blocks 138, 139 that the trigger point has been found.

Next, the switch 150 is used for switching on a treatment position (the switch to the left) and the treatment current is adjusted by using a second auxiliary means 110, 111 such that the feeling of pain remains constant all the time. During the treatment the patient may increase the treatment current using the adjusting second auxiliary means, i.e. controller 110, 111.

This continues until, according to the basic idea of the invention, by block 180 an adequately rapid change is detected in the treatment signal intensity, because the change means that the object tolerates a high current, which, in turn, means that the impedance of the body has risen to a more normal level, which, in turn, means that the electrical conductivity of the object has resumed a more normal, i.e. lower, level owing to the change in metabolism caused by the treatment. The method and arrangement of the invention in FIG. 4 indicate e.g. on a display 190 that the treatment has been effective, or additionally or alternatively terminates the treatment, i.e. finally switches off or significantly lowers the current. In accordance with the object, preferably the second auxiliary means 110 adjusting the treatment current registers by block 180 the change in the treatment current intensity as a function of time and, referring to FIG. 5, monitors the state of the slope of curve K thus provided. When the slope at point P of the graph becomes adequately high, the method indicates that the treatment effect has been appropriately effective. This is based on the fact that as the treatment works, the body becomes electrically less conductive, which means that the point tolerates higher treatment current without the object, i.e. the patient, being disturbed too much any longer.

Figure 5:
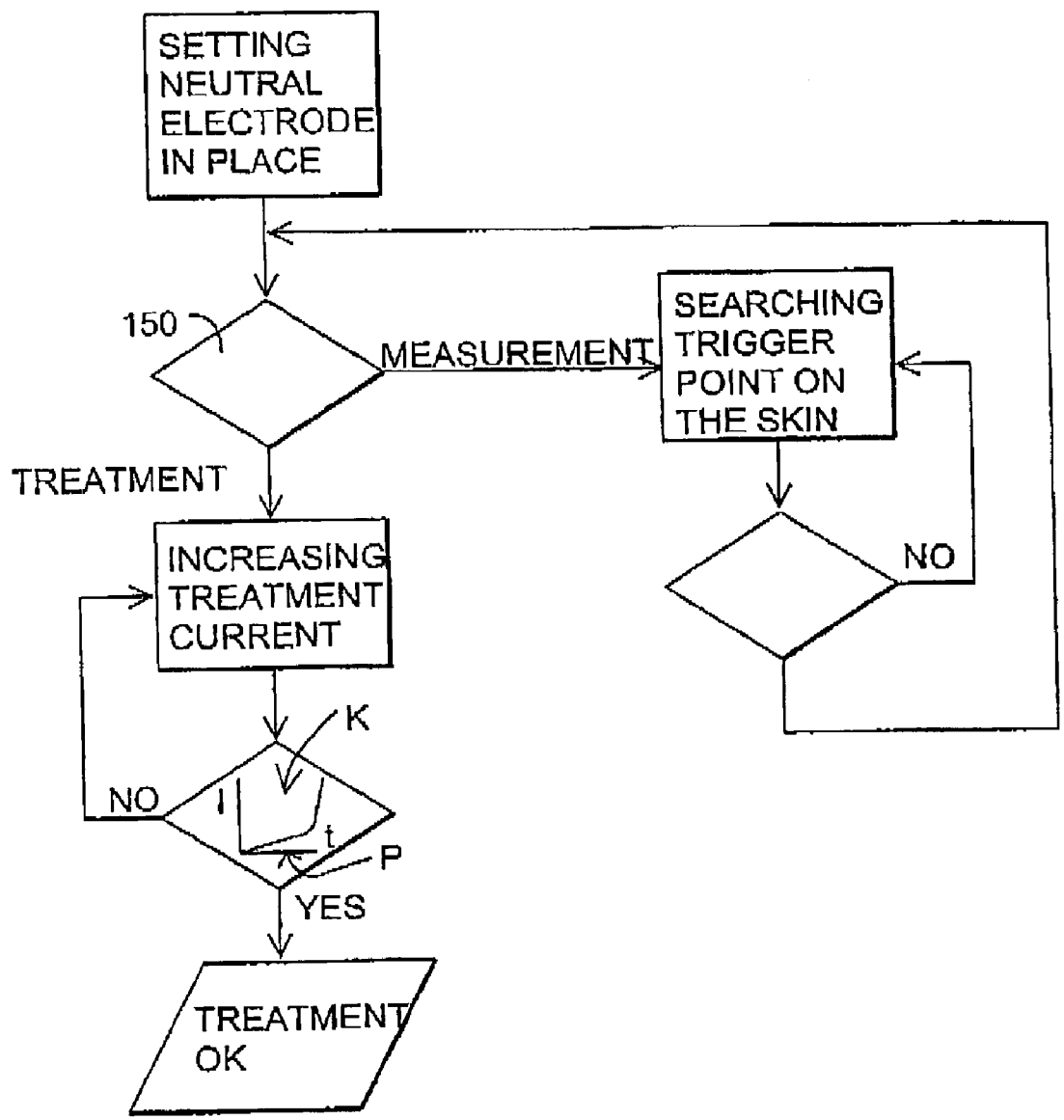
FIG. 5 is a flow diagram showing a method according to the second target of the invention.

The arrangement illustrated in FIGS. 4 and 5 for determining the effect of electrical treatment thus comprises means 180 for monitoring the rate of change in the treatment current and also means 190 connected to the means 180 for indicating that an adequately rapid change has occurred, designating the effect of the treatment. The means 180, 190 are located somewhere in the arrangement, i.e. in the controller 110 or in the treatment device, preferably in the controller 110, which thus also comprises the treatment current intensity adjuster 111 as well.

It is obvious to one skilled in the art that as technology advances, the basic idea of the invention can be implemented in many different ways. The invention and its embodiments are thus not restricted to the examples described above but they may vary within the scope of the claims.

The invention claimed is:

1. A method for determining a suitable treatment frequency and/or intensity of a treatment signal used in electrical treatment, comprising the steps of:
    directing a stimulating electrical signal to an object to produce different reaction types in the object at different intensities of the stimulating electrical signal,
    storing for at least three different reaction types the intensity of the stimulating electrical signal at which a reaction type occurred, wherein one of the reaction types is a motoric reaction type,
    comparing with reference values the electrical signal intensities stored for the different reaction types at least at three different frequencies,
    determining the frequency and/or intensity of the signal at which the intensity of the signal deviates sufficiently from one or more reference values, and
    utilizing the frequency and/or signal intensity found in the process in determining the suitable treatment frequency and/or intensity of the signal.

2. An arrangement for determining a suitable treatment frequency and/or intensity of a treatment signal used in electrical treatment, comprising:
    a generator to generate treatment current at least at three different frequencies,
    an intensity adjuster coupled to the treatment current generator for changing the treatment current intensity,
    a frequency adjuster for the treatment current of the treatment current generator coupled to the treatment current generator and for using at least three different frequencies,
    a reaction registering device for indicating occurrence of at least three different reaction types caused by the treatment current, wherein one of the reaction types is a motoric reaction type,
    a storing device operatively connected to the reaction registering device wherein the treatment current intensity value that prevailed at the moment of occurrence of each of the reaction types is stored,
    a comparing element operatively connected to the storing device for comparing with reference values the electrical signal intensities stored for the different reaction types at least at three different frequencies, and
    an information display device operatively connected to the comparing element for indicating the frequency and/or signal intensity that has been found suitable to provide an adequately large deviation from one or more reference values.

3. A method for determining the effect of electrical treatment, characterized by monitoring the increase in treatment current and when an adequately rapid change in the increase of the treatment current is detected, an indication is given that a sufficient treatment effect has been achieved.

4. An arrangement for determining the effect of electrical treatment, characterized in that the arrangement comprises means for monitoring the rate of change in a treatment current, and means connected to said monitoring means, for indicating that an adequately rapid change has occurred, designating the effect of the treatment.

* * * * *